(12) United States Patent
Zhou et al.

(10) Patent No.: US 9,623,225 B2
(45) Date of Patent: *Apr. 18, 2017

(54) SPECIMEN DISPENSING DEVICE

(75) Inventors: Yuchen Zhou, San Jose, CA (US); Hieu Tieu, San Jose, CA (US); Chao Uei Wahng, Fremont, CA (US); David Hu, Los Altos, CA (US)

(73) Assignee: La Pierres, Inc., San Jose, CA (US)

( * ) Notice: Subject to any disclaimer, the term of this patent is extended or adjusted under 35 U.S.C. 154(b) by 843 days.

This patent is subject to a terminal disclaimer.

(21) Appl. No.: 13/492,852

(22) Filed: Jun. 9, 2012

(65) Prior Publication Data

US 2012/0245730 A1    Sep. 27, 2012

Related U.S. Application Data

(63) Continuation-in-part of application No. 13/317,136, filed on Oct. 11, 2011.

(Continued)

(51) Int. Cl.
*A61M 35/00* (2006.01)
*G06F 19/00* (2011.01)
(Continued)

(52) U.S. Cl.
CPC .......... *A61M 35/003* (2013.01); *A61M 35/00* (2013.01); *G06F 19/3462* (2013.01); *A61F 2007/0087* (2013.01); *A61H 23/00* (2013.01); *A61H 23/006* (2013.01); *A61H 23/0245* (2013.01); *A61H 2201/0207* (2013.01); *A61H 2201/0214* (2013.01); *A61H 2201/10* (2013.01);

(Continued)

(58) Field of Classification Search
CPC .. A47K 5/1217; B67D 7/0044; B67D 7/0046; B05B 11/3081; B05B 11/3082; B65D 83/66; B65D 83/68; B65D 83/682; A61M 35/003; A61M 2005/14208; A61M 11/00; A61F 2007/0087; A61F 7/00; A61F 2007/00; A61H 2201/105; A61H 7/00; A61H 7/001; A61H 7/002; A61H 7/003; A61H 7/004; A61H 7/005; A61H 23/00; A61H 23/02; A61H 23/0245; A61H 2201/0119; A61H 2201/0153; A61H 2201/0157; A61H 2201/02; A61H 2201/02; A61H 2201/0221; A61H 2201/0285; A61H 2201/1207; A61H 2201/16; A61H 2201/50; A61H 2201/5007; A61H 2201/501; A61H 2201/5023; A61H 2201/5097

See application file for complete search history.

(56) References Cited

U.S. PATENT DOCUMENTS 4,984,568 A    1/1991  Persaud
5,622,692 A *  4/1997  Rigg ................. A61B 5/442
                                                    356/402

(Continued)

*Primary Examiner* — Justine Yu
*Assistant Examiner* — Tu Vo
(74) *Attorney, Agent, or Firm* — Leon E. Jew; Bing K. Yen

(57) ABSTRACT

This invention describes an electronic skin care device including therein a specimen dispenser. Specimens are dispensed from the device after the specimen information stored in the storage component located in the dispenser is processed by the device. The user skin information stored in another storage component located in the device may also be utilized so that dispensed specimens have desired properties for the user's skin care need.

11 Claims, 13 Drawing Sheets

Related U.S. Application Data

(60) Provisional application No. 61/456,164, filed on Nov. 2, 2010.

(51) Int. Cl.

| | |
|---|---|
| *A61H 23/00* | (2006.01) |
| *A61H 23/02* | (2006.01) |
| *A61M 37/00* | (2006.01) |
| *A61N 5/06* | (2006.01) |
| *A61F 7/00* | (2006.01) |
| *A61N 1/04* | (2006.01) |
| *A61N 1/32* | (2006.01) |

(52) U.S. Cl.
CPC . *A61H 2201/5097* (2013.01); *A61M 37/0092* (2013.01); *A61N 1/0408* (2013.01); *A61N 1/328* (2013.01); *A61N 5/0616* (2013.01)

(56) References Cited

U.S. PATENT DOCUMENTS

| | | | | |
|---|---|---|---|---|
| 5,785,960 A * | 7/1998 | Rigg | ............ | A45D 44/005 366/160.1 |
| 5,903,465 A * | 5/1999 | Brown | ............ | A45D 44/005 700/242 |
| 6,437,866 B1 * | 8/2002 | Flynn | ............ | A45D 44/005 356/326 |
| 6,510,366 B1 * | 1/2003 | Murray | ............ | A45D 44/00 700/233 |
| 6,715,642 B2 * | 4/2004 | Engel | ............ | A45D 34/04 222/132 |
| 6,747,561 B1 * | 6/2004 | Reeves | ............ | 340/573.1 |
| 6,779,686 B2 * | 8/2004 | Bartholomew | ............ | A45D 44/00 222/1 |
| 6,782,307 B2 * | 8/2004 | Wilmott | ............ | A61K 8/044 700/233 |
| 6,935,386 B2 * | 8/2005 | Miller | ............ | B01F 13/1055 141/104 |
| 7,347,344 B2 * | 3/2008 | Engels | ............ | B01F 13/1058 222/1 |
| 7,427,273 B2 * | 9/2008 | Mitsui | ............ | 601/2 |
| 7,562,680 B2 * | 7/2009 | Khoo | ............ | B01F 13/1055 141/192 |
| 7,690,405 B2 * | 4/2010 | Miller | ............ | B01F 13/1055 141/104 |
| 7,916,013 B2 * | 3/2011 | Stevenson | ............ | 340/539.12 |
| 8,224,481 B2 * | 7/2012 | Bylsma | ............ | A61M 5/1413 222/129.4 |
| 8,523,791 B2 * | 9/2013 | Castel | ............ | 601/15 |
| 2005/0191252 A1 | 9/2005 | Mitsui | | |
| 2006/0149169 A1 * | 7/2006 | Nunomura et al. | ............ | 601/2 |
| 2006/0237002 A1 * | 10/2006 | Bonney et al. | ............ | 128/200.23 |
| 2006/0276731 A1 | 12/2006 | Thiebaut et al. | | |
| 2008/0139974 A1 * | 6/2008 | Da Silva | ............ | 601/3 |
| 2009/0118684 A1 * | 5/2009 | Da Silva et al. | ............ | 604/290 |
| 2009/0210322 A1 * | 8/2009 | Stark | ............ | A61Q 1/02 705/26.1 |
| 2009/0306577 A1 * | 12/2009 | Akridge et al. | ............ | 604/20 |
| 2009/0318853 A1 * | 12/2009 | Reed et al. | ............ | 604/22 |
| 2010/0213212 A1 * | 8/2010 | Custodis et al. | ............ | 222/113 |
| 2011/0220139 A1 * | 9/2011 | Samain | ............ | 132/200 |
| 2011/0251526 A1 | 10/2011 | Kim | | |
| 2011/0251537 A1 | 10/2011 | Yeo | | |
| 2011/0288680 A1 * | 11/2011 | Samain et al. | ............ | 700/239 |

\* cited by examiner

SPECIMEN DISPENSING DEVICE

CROSS REFERENCE TO RELATED APPLICATIONS

This application is a continuation-in-part of and claims the benefit of priority to U.S. patent application Ser. No. 13/317,136, entitled "Integrated skin-treatment specimen dispenser with electrical interface," filed on Oct. 11, 2011, which claims the benefit of domestic priority to U.S. provisional application Ser. No. 61/456,164 filed on Nov. 2, 2010, the content of which being incorporated in its entirety by reference herein.

The application is also related to (1) U.S. patent application Ser. No. 12/925,017, entitled "Ultrasonic device with integrated specimen dispenser," filed on Oct. 12, 2010, (2) U.S. patent application Ser. No. 12/932,316, entitled "Massaging device with multiple ultrasonic transducers," filed on Feb. 22, 2011, (3) U.S. patent application Ser. No. 13/317,203, entitled "Piezoelectric element driver", filed on Oct. 11, 2011, and (4), U.S. patent application Ser. No. 13/396,381, entitled "Skin treatment device with an integrated specimen dispenser", filed on Feb. 14, 2012, the contents of which are incorporated in their entirety by reference herein.

FIELD OF THE INVENTION

The present invention generally relates to electrical and electronic skin care technology and more particularly to a skin care specimen dispenser.

BACKGROUND OF THE INVENTION

Skin care products in today's market are generally in the forms of lotion, cream, serum, powder, solid, gel, liquid or other physical forms. It is a universal practice in the commercially available skin care products that these products are marketed and provided to users in these forms without specification or means that are designed to meet the specific skin condition of different individual users. Consequently, the different skin types of different users after using the same skin care product can usually produce different skin care results, even though the functional ingredients of the same product are identical. For example, a skin care product marketed as "anti-aging" usually targets the aging signs of the facial skin, including wrinkles, age spots, fine lines and puffy eyes, etc. By using a product targeting to reduce multiple signs of aging, which generally includes multiple active ingredients, with a single or a group of ingredients functioning to reduce certain type of aging sign, a user with stronger wrinkles or a user with stronger puffy eyes may not experience the same level of effectiveness of aging sign reduction as compared to a normal user with a more evenly weighted aging signs.

The inventors realize that the way that the existing skin-care products are marketed and the method that is generally practiced by users on daily basis is lack of the ability to customize the skin care product composition to match to the skin condition and skin care need of each individual. By enabling this ability to customize the skin care product composition to each individual skin care need, more effectiveness from the skin care product and better skin care result shall be achieved than the existing method of using existing skin-care products.

It is an object of this invention to provide a specimen dispensing device that enables the customizability of skin care products.

It is another object of this invention to provide a specimen dispensing device that enables the customizability of other health care or personal products.

SUMMARY OF THE INVENTION

In this invention, we described a specimen dispensing device that can achieve individually customizable skin care product. Similar method and device can also be used for other health care and personal care needs, as long as the ability to individually customize a specimen can make a beneficial improvement in the health care or personal care effectiveness and provide better care result.

The specimen dispensing device for dispensing one or more types of specimen to a target skin area of a human being according to this invention includes: a device body; a dispenser containing the specimen; a specimen outlet existing on the device body, the outlet being operatively connected to the dispenser, where the specimen passes through during a dispensing operation; at least one electrical contact being electrically connected to an electronic circuit included in the dispenser; at least one first information storage component located in the dispenser storing first type of information; a control unit containing electronic circuits and embedded software; an electrical connection between the dispenser and the control unit; at least one second information storage component located in the control unit storing second type of information; and at least one information processing component in the control unit controls the dispensing of specimen from the dispenser by processing the first type and second type of information.

The dispenser can be a removable and replaceable dispenser; a refillable dispenser; a disposable and for one-time use only dispenser; a dispenser having multiple sub-dispensers containing same or different specimens, the sub-dispensers being individually selectable to dispense specimen therein; a dispenser with multiple specimen compartments containing same or different specimens, each of the compartments being individually selectable to dispense specimen therein; a dispenser that resides within the device body; or a dispenser that is externally attached to the device body.

The specimen can be any of: liquid, gel, serum, cream, lotion, paste and powder. It can be used for a variety of treatments such as biological body area, body function, organ, skin, bone, tissue and cell.

The specimen is dispensed from the dispenser by any means of: a manually exerted or a pre-loaded force to the dispenser, wherein the control unit controls the dispensing by limited the amount of specimen being dispensed from one or more of the specimen containing compartments or sub-dispensers; an electrically powered driving mechanism that is part of the dispenser and operated by the control unit; and an electrically powered driving mechanism that is part of the device body and electrically controlled by the control unit.

The first type of information is related to the specimen, and is further related to how the specimen is dispensed, including but not limited to any of: information of the specimen such as: specimen brand, name, type, original, composition, production date and expiration date, specimen level within the dispenser and ordering information, number of sub-dispensers and compartments, information of specimen within sub-dispensers and compartments; information of optimal or pre-set operational mode of the different sub-dispensers or different specimen compartments within a single dispenser, where the operational mode can be, but not limited to, timing and/or flow speed of specimen application from each different dispenser or each different compartment, amount of specimen to be dispensed from each different dispenser or each different compartment; information of historic usage data of the device, the dispenser and specimen; information that is created or input by the user, manufacturer, or a health care professional; information transferred from the control unit; biometrics information of the user; and information enabling anti-fake, anti-piracy, authenticity confirmation.

The first type of information is transmitted to the information processing component in the control unit by using a standardized protocol. The protocol can be designed such that different specimen information in any individual compartment or individual sub-dispenser is arranged in the same digital format. The same digital format can be an ordered number and/or character sequence of information that contains an allocate space in a sequence for any of the possibly needed information of any given specimen to be dispensed from the device. The protocol can be used to standardize the communication between any specimen dispenser made by different vendors and any dispensing devices made by other vendors to achieve compatibility and to reduce cost of operation.

The first information storage component can be any of: a digital data storage device, such as flash memory, phase-change memory, resistive RAM, MRAM, DRAM, SRAM, magnetic data storage device; an analog data storage device; an optically recognizable markings such as letters, numbers, bar code, graphics, color patterns; RF ID; physical indentations or protrusions and chemicals; a hard coded dispensing regulation component such as an electronic chip, a circuit component, a mechanical valve or a non-volatile memory.

The second type of information is related to the target skin area of a human being, such as device operation data, user skin information data, user personal and biometrics information, dispenser identification data, date, time, season, weather and other user-specific data, application schedule and reminder message:

The second information storage component can be any of: a digital data storage device such as flash memory, phase-change memory, resistive RAM, MRAM, DRAM, SRAM, magnetic data storage device; an analog data storage device; an optically recognizable markings such as letters, numbers, bar code, graphics, color patterns; RF ID; physical indentations or protrusions, and chemicals.

The control unit includes means for displaying information to a user through visual, skin contact or sound effects; means for receiving the first type of information stored in the first information storage component and the second type of information stored in the second information storage component; and means for processing the first type information and the second type of information by the information processing component and for providing instructions to control the dispenser to dispense the specimen in a specific manner. The control unit may further include: means for sending data to be stored in the dispenser, wherein data stored in the container is retrievable; means or providing user interface, power supply and charging functions; and means for sending messages wirelessly to a second device such as, but not limited to a computer, a mobile device, a smart phone, or a data center.

The information processing component includes embedded software for processing the first type and second type of information. The embedded software, first type of information and second type of information may be retrieved or updated through a data interface within the device. The retrieval and update can be done by any of, a computer, a mobile device, a smart phone, or a data center. The data interface can be any of: a wireless transmitter/receiver within the control unit; a data communication component that utilizes the wireless charging circuitry to transmit digital or analog data; and one or more electrical contacts that connect to the control unit.

The dispensing surface of the device is a skin treatment member which can produce any of: ultrasonic vibration, sub-sonic vibration, electrical voltage or current application, heating, cooling, light emission, air blowing, brushing, tapping, shaking, pulsating or scrubbing.

DETAILED DESCRIPTION OF THE INVENTION

Figure 1:
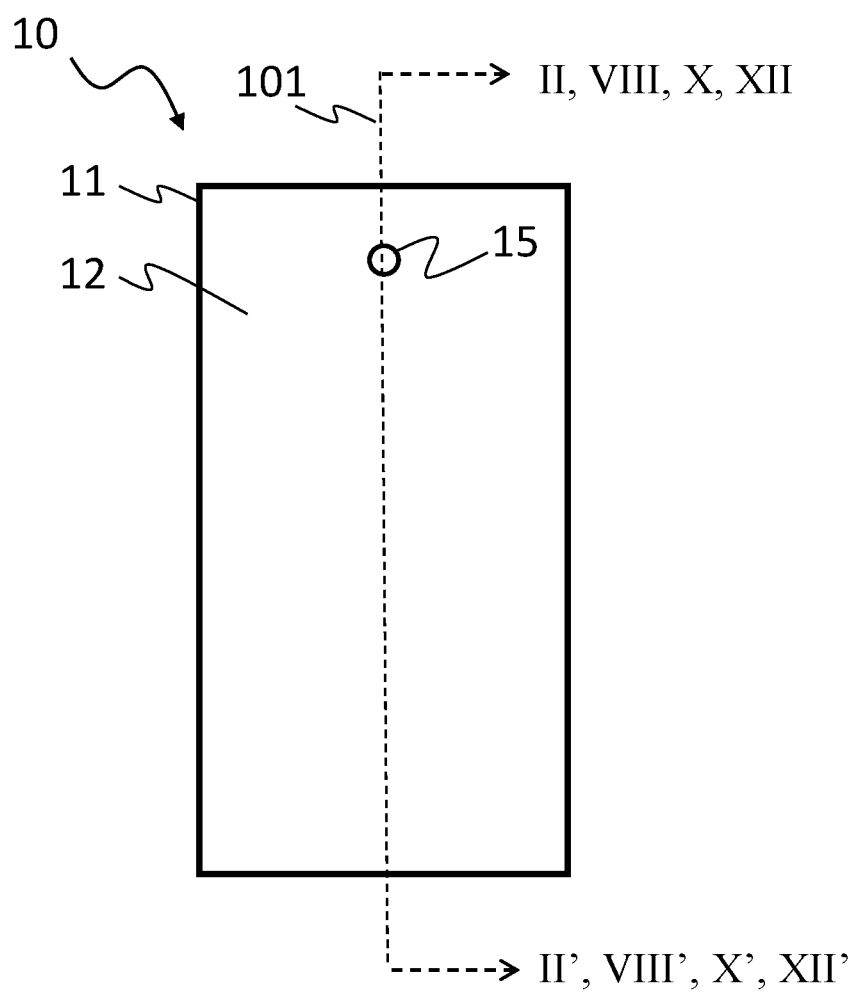
FIG. 1 is a schematic diagram illustrating a front view of the specimen dispensing device according to the first preferred embodiment of the present invention.

While the present invention may be embodied in many different forms; designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

First Preferred Embodiment

Figure 2:
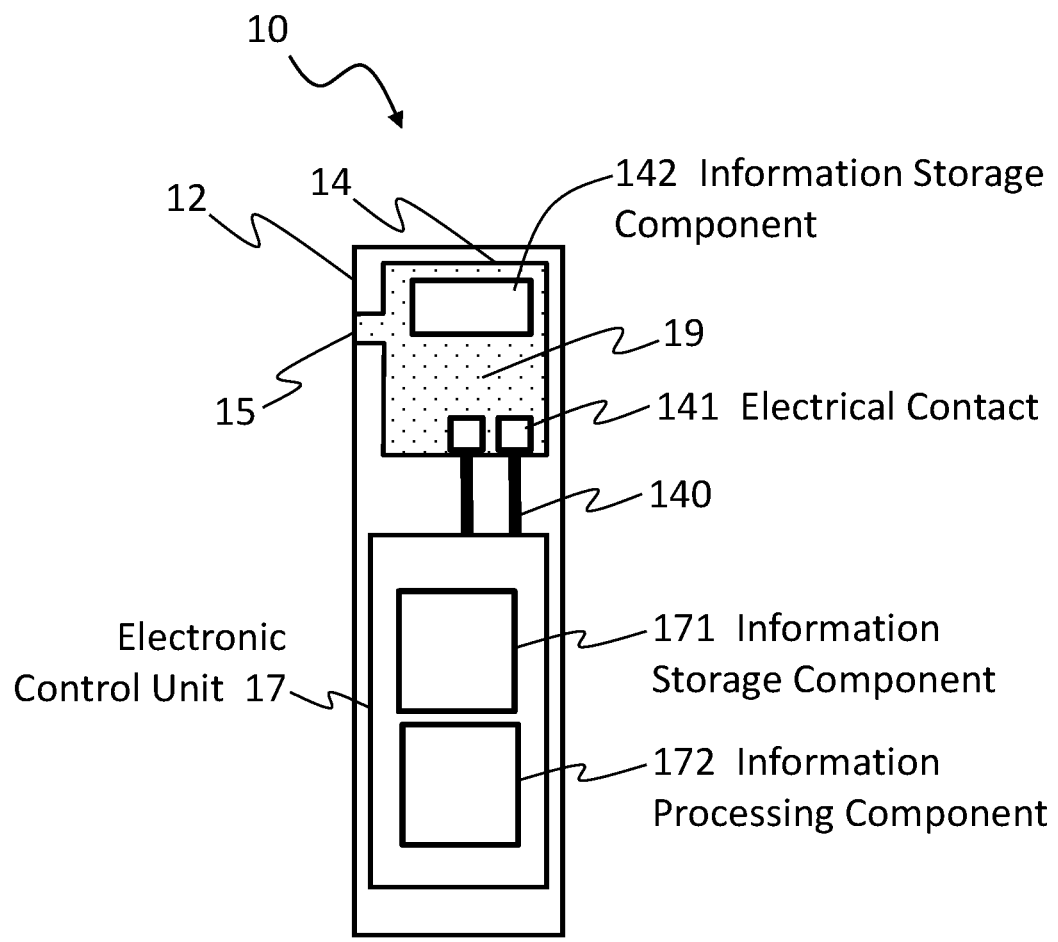
FIG. 2 is a schematic diagram illustrating a cross-sectional view of the specimen dispensing device of FIG. 1.

The first preferred embodiment of the present invention is illustrated in FIG. 1 and FIG. 2, where a specimen dispenser is integrated within a specimen dispensing device 10. FIG. 1 is a schematic diagram illustrating a front view of the specimen dispensing device 10, where the outside rectangle shape is shown merely for description purpose and in practice can be any other shapes as needed. FIG. 2 is a schematic diagram illustrating a cross-sectional view along the center line 101 of FIG. 1.

The first preferred embodiment of the specimen dispensing device, as illustrated in FIG. 1 and FIG. 2, which represents the best mode of this invention, contains the following components or aspects: a device body 11, a dispensing surface 12, a dispenser 14, at least one electrical contact 141, at least one type of information storage component 142 included in the dispenser 14, a specimen outlet 15, an electronic control unit 17, an electrical interface 140, at least one information storage component 171 included in the control unit 17, and at least one information processing component 172.

The device body 11 provides a case or housing for the dispenser and the internal electronics (Not shown in FIG. 1 and FIG. 2). It can be made of metal, alloy, glass, plastics or any other solid materials.

The dispensing surface 12 is a high-quality smooth surface which allows the dispensed specimen to temporarily reside upon before transferring to target skin area. However, in other embodiment, the specimen can be dispensed directly onto the target skin are without staying on surface 12, for example through a spray function.

The skin treatment specimen dispenser 14, which can be in any shape, contains skin treatment specimen 19 which can be, but not limited to, liquid, gel, cream, paste, serum, lotion and powder.

The at least one electrical contact 141 resides on the dispenser 14. It is electrically connected to the electrical circuits that are parts of dispenser 14.

The at least one type of information storage component 142 included in the dispenser 14, which is not shown in FIG. 1 and FIG. 2, stores information concerning how the specimen 19 to be dispensed. The information can be, but not limited to, dispensing amount, dispensing speed, timing of dispense and specimen information.

The specimen outlet 15 is one hole or an array of holes, which is located on the surface 12 and is embedded in the front of the body 11. In operation, the skin treatment specimen 19 is dispensed through the outlet 15.

The electronic control unit 17 contains electrical circuits, electronic components and necessary software or firmware placed in the device body 11.

The electrical interface 140 is located between the dispenser 14 and the electronic control unit 17 such that the dispensing of specimen 19 from the dispenser 14 can be entirely or partially controlled by the electronic control unit 17.

The at least one information storage 171 component included in the control unit 17, which is not show in FIG. 1 and FIG. 2, is located in and electronically coupled to the control unit 17. It stores information related to how to control the dispensing of specimen 19 from dispenser 14, such information can be, but not limited to, software or firmware, device operation data, user skin information data, user personal and biometrics information, dispenser identification data, date, time, season, and other user-specific data such as preference, schedule, reminder message and avoidance. Such stored information may be updated as needed, by user or by a health care professional.

The at least one information processing component 172, which is not shown in FIG. 1 and FIG. 2, is also located in and electronically coupled to the control unit 17. It retrieves information stored in the information storage 142 component and the information stored in the information storage component 171, processes all the retrieved information and provides instructions to control the dispensing of specimen 19 from the dispenser 14.

The electronic control unit 17 controls the dispensing of specimen 19 from dispenser 14, through outlet 15, and onto surface 12. The control unit 17 may also provide user interface, power supply and charging functions. Additionally, the electronic control unit 17 may send electrical signals to the specimen dispenser 14 or receives electrical signals from the specimen dispenser 14, to achieve required skin treatment procedure through electrical interface 140 that electrically connects to the electrical contacts 141 on dispenser 14.

The dispenser 14 may have any of the below features: (1) it can be removable, in other words, it may be taken out and installed back into the device 10 by the user; (2) the specimen 19 may be replenished within dispenser 14 by the user, or a health care professional, after depletion of the specimen during usage, i.e. dispenser 14 may be re-used; (3) dispenser 14 may be disposable and for one-time use only, where specimen 19 is pre-filled within the dispenser before usage; (4) the dispenser 14 can be configured as having multiple sub-dispensers containing same or different specimens such that the sub-dispensers can be individually selected to dispense contained specimen; (5) the dispenser 14 can be configured as a single dispenser with multiple specimen compartments that may contain same or different specimens, such that each compartment within the dispenser can be individually selected and dispense specimen; (6) the dispensing of the specimen 19 is fulfilled by a manually exerted or a pre-loaded force to the dispenser, upon which a pressure generation component that is part of the dispenser, for example a lead, a lever, a gauge, a cap, a piston, a spring, compressed air or a stretched porch, forces the specimen 19 to flow out of the dispenser through the outlet 15, where the control unit 17 controls the dispensing by limiting the amount of specimen being dispensed from one or more of the specimen containing compartments or sub-dispensers; (7) the dispensing of the specimen 19 is fulfilled by an electrically powered driving mechanism that is part of the dispenser and operated by the electrical interface 140 located within the device 10 body; (8) the dispensing of the specimen 19 is fulfilled by an electrically powered driving mechanism that is a part of the device and electrically controlled by the control unit 17. The driving mechanism provides mechanical force to dispenser 14 to make the specimen 19 flow out of the dispenser through the outlet 15.

In other words, the dispenser 14 can be any of: a removable and replaceable dispenser; a refillable dispenser; a disposable and for one-time use only dispenser; an integrated dispenser having multiple sub-dispensers containing same or different specimens, the sub-dispensers being individually selectable to dispense specimen therein; and an integrated dispenser with multiple specimen compartments containing same or different specimens, each of the compartments being individually selectable to dispense specimen therein.

Figure 3:
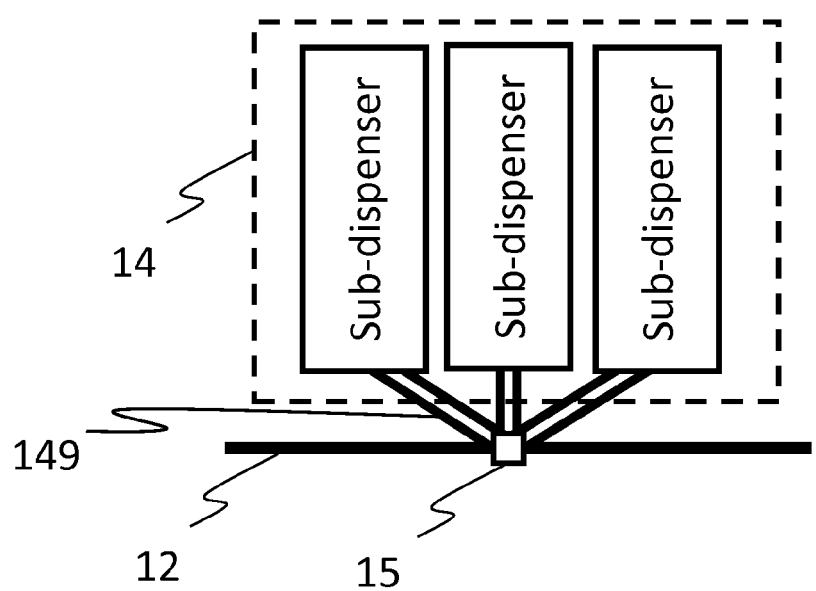
FIG. 3 is a schematic diagram illustrating a specimen dispenser having multiple sub-dispensers.

FIG. 3 is a schematic diagram illustrating a specimen dispenser 14 which has multiple sub-dispensers. The sub-dispensers are physically separated dispensers by themselves. Each sub-dispenser has a conduit 149 that connects to the outlet 15 on the surface 12, where the conduits 149 converge at or in close proximity to the outlet 15. Before the convergence point, the conduits 149 are separated to avoid cross-contamination of the specimen from different sub-dispensers. The sub-dispensers are referred to as dispenser 14 as a whole entity. However, when dispenser 14 is replaced, all sub-dispensers may be replaced together, or replaced individually.

Figure 4:
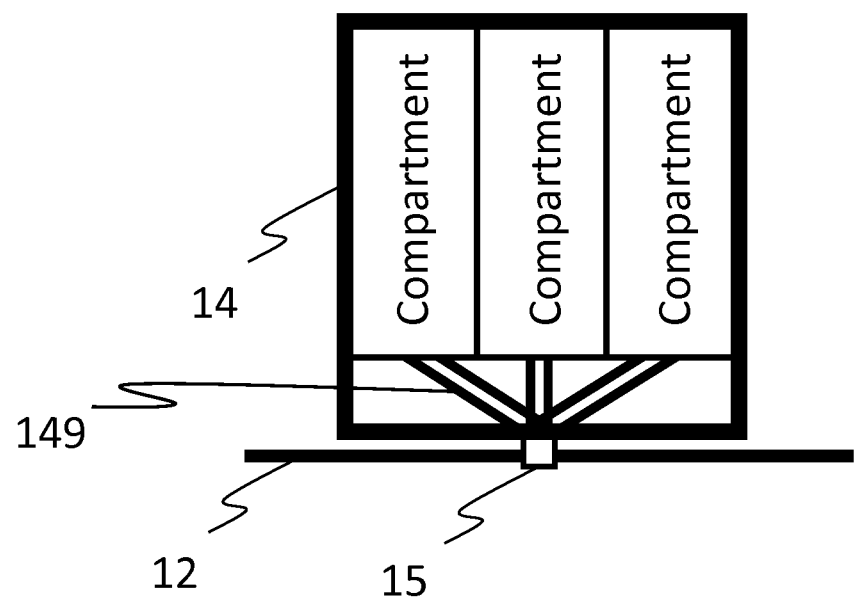
FIG. 4 is a schematic diagram illustrating a specimen dispenser having multiple compartments.

FIG. 4 is a schematic diagram illustrating a specimen dispenser 14 having multiple compartments. The dispenser 14 has a physical containment body where the compartments reside. During specimen dispensing, the compartments may function similar as independent dispensers by themselves. Each compartment has a conduit 149 that connects to the outlet 15 on the surface 12, where the part of or entire conduit 149 may exist within the dispenser body. The conduits 149 from different compartments converge at or in close proximity to the outlet 15. Before the convergence point, the conduits 149 are separated to avoid cross-contamination of the specimen from different sub-dispensers. When the dispenser 14 is replaced, specimens in all compartments are replaced together.

The at least one information storage component 142 included in the dispenser 14 can store any of the following listed information, but not limited to: (1) data about the specimen contained within the dispenser 14, which can be, but not limited to, specimen brand, name, type, origin, composition, production date and expiration date, specimen level within the dispenser and ordering information, number of sub-dispensers and compartments, information of specimen within sub-dispensers and compartments; (2) data about optimal or pre-set operational mode of the different sub-dispensers or difference specimen compartments within a single dispenser, where the operational mode can be, but not limited to, timing and/or flow speed of specimen application from each different sub-dispenser or each different compartment, amount of specimen to be dispensed from each different sub-dispenser or each different compartment; (3) information about historic usage of the device, the dispenser and specimen; (4) information that is created or input by the user; (5) information transferred from the control unit 17; (6) biometrics information of the user; and (7) anti-fake, anti-piracy, authenticity confirmation.

The information storage component 142 included in the dispenser 14 can be in the form of, but not limited to: (1) digital data storage device, which can be any of: flash memory, phase-change memory, resistive RAM, MRAM, DRAM, SRAM, magnetic data storage device; (2) analog data storage device; (3) optically recognizable markings which can be any of: letters, numbers, bar code, graphics, color patterns; (4) RF ID; (5) physical indentations or protrusions; and (6) chemicals.

The electronic control unit 17 may receive data stored in the dispenser 14 to display information to the user through visual, skin contact or sound effects. Alternatively, the electronic control unit 17 may receive data stored in the dispenser 14 to dispense specimen 19 a specific manner determined by the information stored in the received data. The electronic control unit 17 may also send messages, wirelessly to an external device such as, but not limited to, a computer, a mobile device, a smart phone, or a data center.

The communication between the information storage component 142 and the control unit 17, especially when data stored in the information storage component 142 of the dispenser 14 are transmitted to the control unit 17, can be achieved by using a standardized protocol. Such protocol can be designed such that the different specimen information in any individual compartment or individual sub-dispenser is arranged in the same digital format and transmitted to the control unit 17 in sequence or in parallel. The same digital format can be an ordered number and/or character sequence of information that contains an allocate space in the sequence for any of the possibly needed information of any given specimen to be dispensed from the dispensing device. Such protocol can also be used to standardize the communication between any specimen dispensers made by different vendors and any dispensing devices made by other vendors, such that they can be easily made compatible and reduce cost of operation.

The information processing component 172 included in the control unit 17 may contain embedded programs that utilize all the information stored in the information storage components 142 and 171 in the dispenser 14 and in the control unit 17 to operate and control the serum dispensing from the dispenser 14. Such embedded programs may also be updated for better function from time to time. Update of the information stored in the information storage component 171 of the control unit 17 and the programs in the information processing component 172 can be achieved using a data connection to a computer, a mobile device, a smart phone or a data center. The data connection is preferably through a wireless interface such as wireless internet, Bluetooth or other digital or analog wireless interface. Wireless data transmission can be achieved by a data transmission interface controlled by the control unit 17. Such interface may be an embedded communication component within the control unit 17, like a wireless antenna, or sharing of the wireless charging electronics, where charging and data transmission can be achieved at different frequencies through the same circuit. Otherwise, such update can be done through a direct electric wire connection through electrical contacts that connect to the control unit 17 and can be connected externally.

The electronic control unit 17 may send data to be stored in the dispenser's information storage component 142. The dispenser 14 may be recovered by the manufacture and data stored within the dispenser 14 may be retrieved.

Multiple types of device operations can be realized based on the first preferred embodiment of the specimen dispensing device of the current invention.

Figure 5:
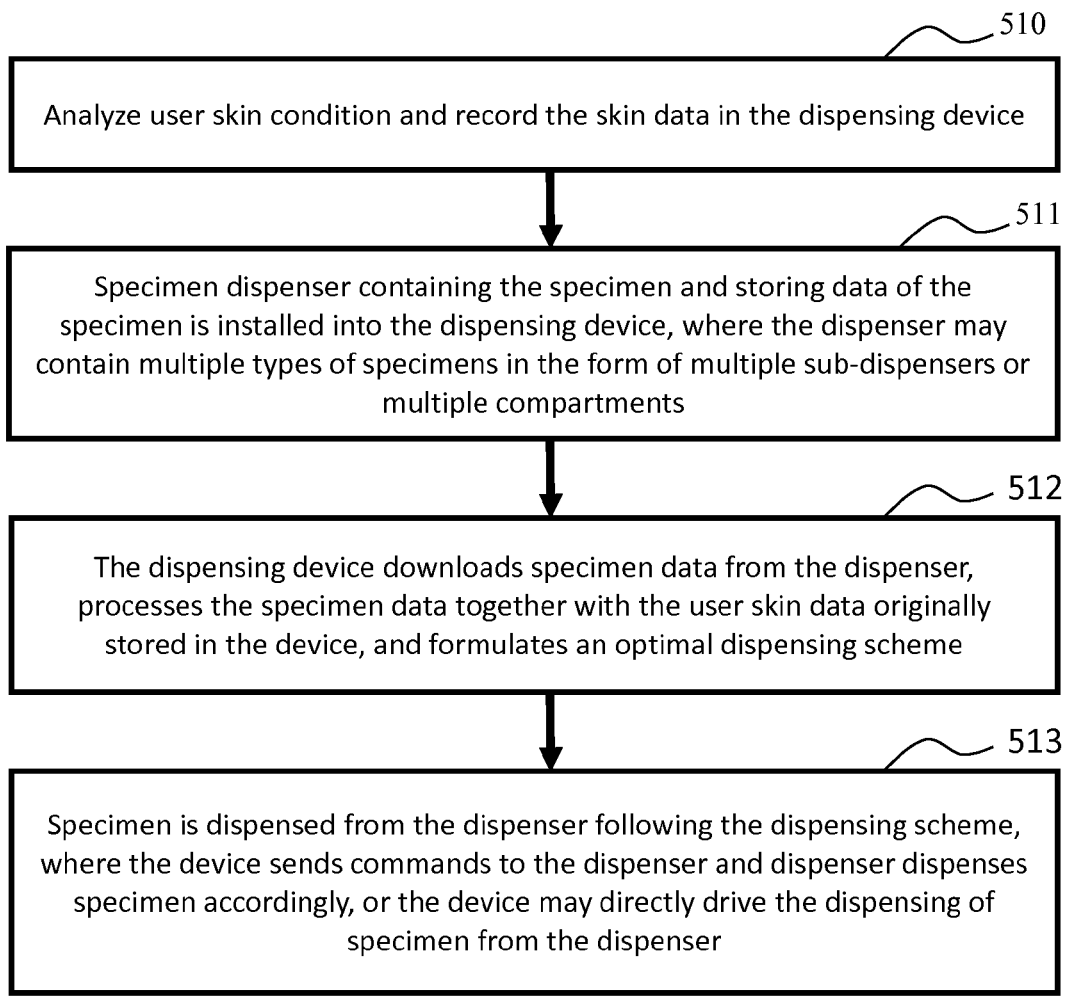
FIG. 5 is a flow diagram illustrating a process of operation of the specimen dispensing device according to the first preferred embodiment of the present invention.

FIG. 5 is a flow diagram illustrating a process of operation according to the first preferred embodiment. Referring to FIG. 2 and FIG. 5, the information storage component 142 contains information related to the specimen, and the information storage component 171 contains information related to how to control the dispensing of the specimen 19 from the dispenser 14, such information can be, but not limited to, user skin information data, user personal and biometrics information, dispenser identification data, date, time, season, and other user-specific data such as preference, schedule, reminder message and avoidance.

The process of operation as illustrated in FIG. 5 includes steps of:

Step 510: storing data about the user's skin condition in the dispensing device.

Step 511: storing data of the specimen in the dispensing device.

Step 512: calculating an optimal dispensing scheme according to the specimen data and the user skin data.

Step 513: dispensing specimen according to the dispensing scheme.

Figure 6:
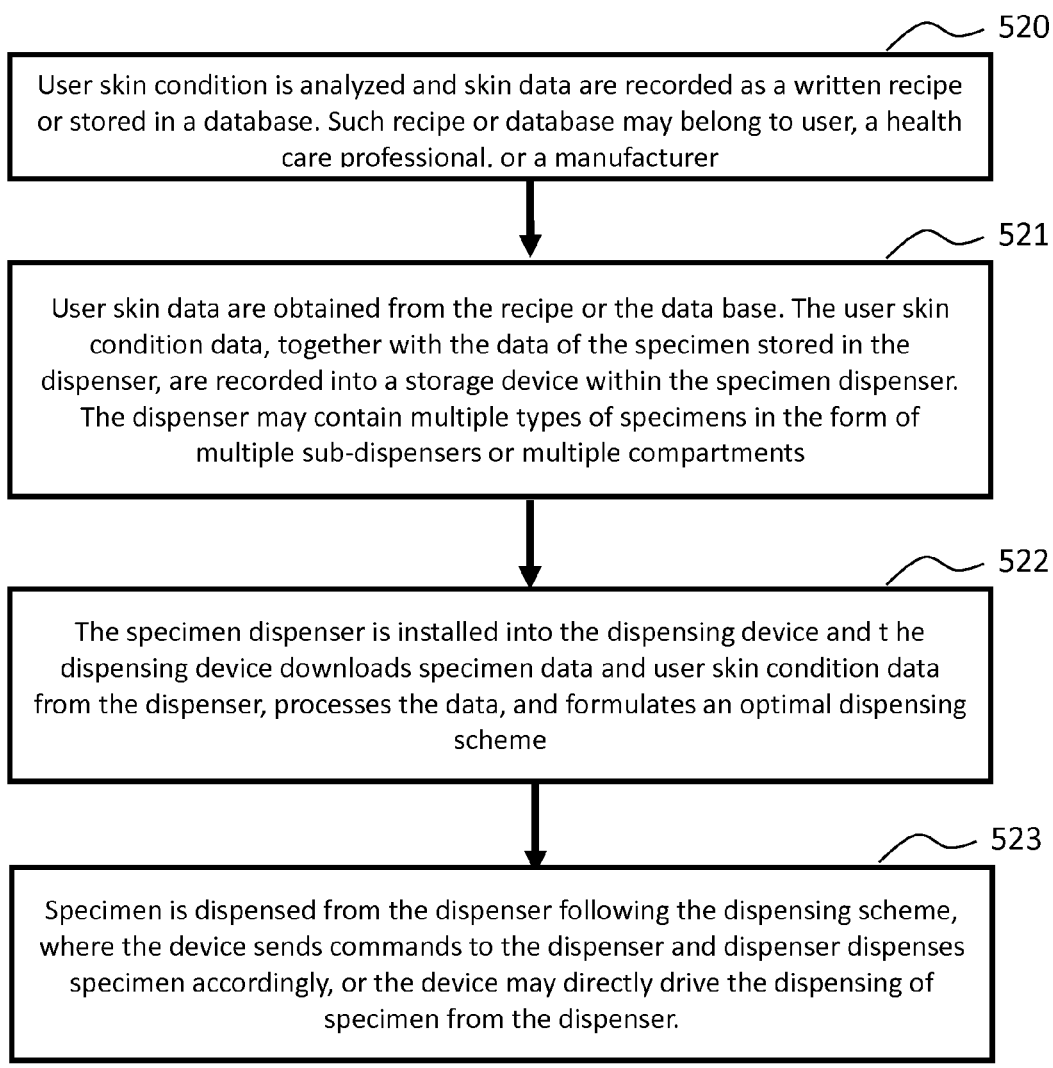
FIG. 6 is a flow diagram illustrating another process of operation of the specimen dispensing device according to the present invention.

FIG. 6 is a flow diagram illustrating another process of operation according to the first preferred embodiment. Referring to FIG. 2 and FIG. 6, the information storage component 142, in addition to containing information related to the specimen, may also contain information related to how to control the dispensing of the specimen 19 from the dispenser 14, such information can be, but not limited to, user skin information data, user personal and biometrics information, dispenser identification data, date, time, season, and other user-specific data such as preference, schedule, reminder message and avoidance. Such stored information may be configured and updated by user, by manufacturer or by a health care professional. In such embodiment, the information storage component 171 can store any of, but only limited to, device operation data, dispenser operation data, software, firmware or data received from the dispenser 14.

The process of operation as illustrated in FIG. 6 includes the steps of:

Step 520: storing user's skin data as a written recipe or storing the data in a database. The recipe or database may belong to the user, a health care professional, or a manufacturer.

Step 521: retrieving the user skin data from the recipe or the data base. The user skin condition data, together with the data of the specimen stored in the dispenser, are recorded into a storage device within the specimen dispenser. The dispenser may contain multiple types of specimens in the form of multiple sub-dispensers or multiple compartments.

Step 522: after the specimen dispenser being installed into the dispensing device, downloading specimen data and user skin condition data from the dispenser and calculating for an optimal dispensing scheme.

Step 523: dispensing specimen from the dispenser according to the dispensing scheme, where the device sends commands to the dispenser and dispenser dispenses specimen accordingly, or the device may directly drive the dispensing of specimen from the dispenser.

Figure 7:
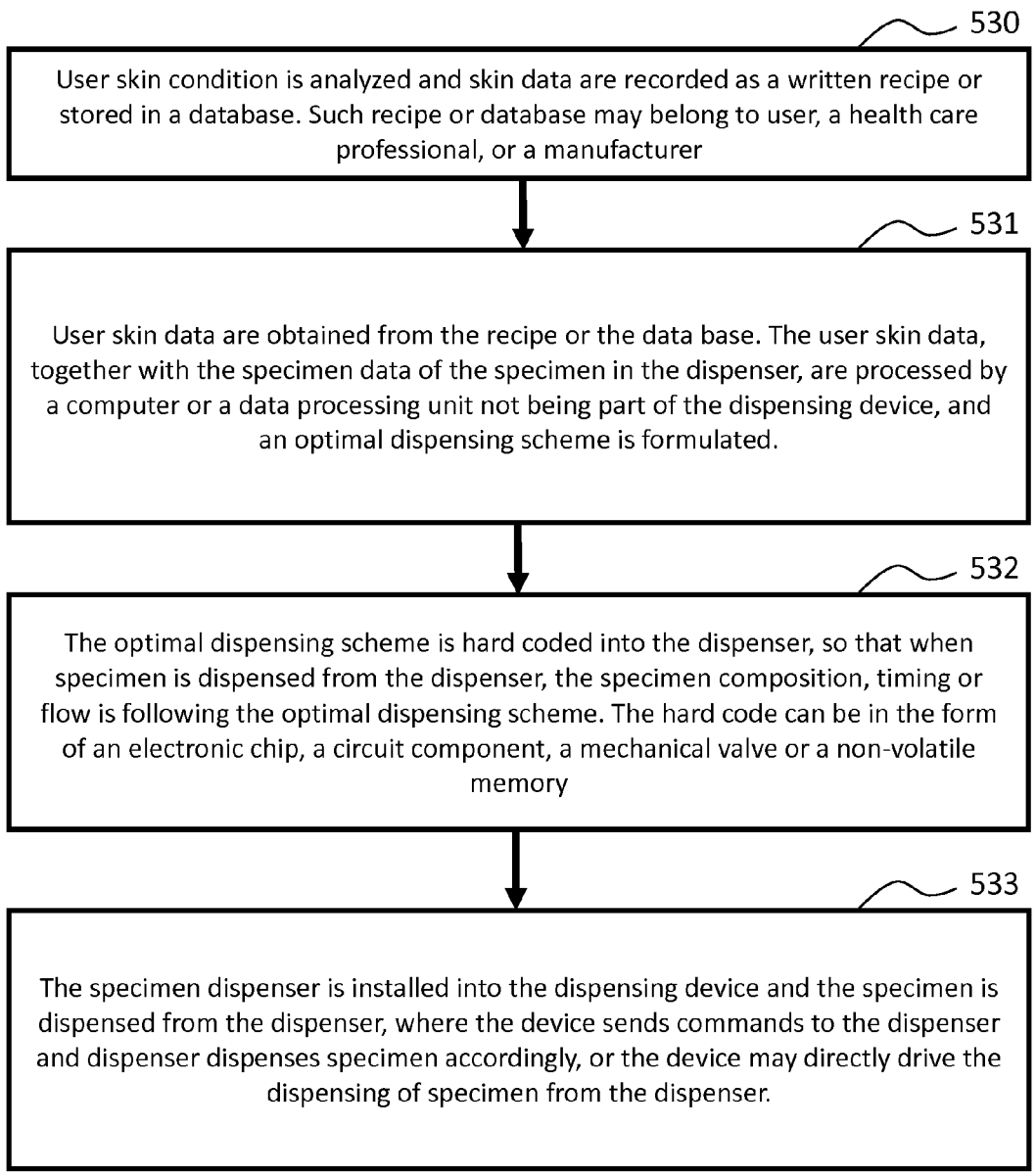
FIG. 7 is a flow diagram illustrating another process of operation of the specimen dispensing device according to the present invention.

FIG. 7 is a flow diagram illustrating another process of operation according to the first preferred embodiment. Now referring to FIG. 2 and FIG. 7, the information storage component 142 is in the form of a hard coded dispensing mechanism, which regulates the specimen dispensing from the dispenser 14, or any sub-dispenser and any compartment of the dispenser 14, by any of: dispensed specimen composition, outflow speed and dispensing timing. Such hard coded dispensing mechanism is configured with the capacity to store the specimen data, the user data, user skin condition data and any other type of information relating to the proper dispensing of the specimen to meet the user's skin care need. In such configuration, the information storage component 171 can store any of, but not limited to, device operation data, dispenser operation data, software, firmware or data received from the dispenser 14. One of such example is that manufacturer acquires user skin condition and configures the dispenser, electrically or mechanically, in such a way that, when specimen is dispensed from the dispenser when installed in the device, the dispensed specimen is in correct composition to match the user's skin area and condition. The hard code can be, but not limited to, an electronic chip, a circuit component, a mechanical valve or a non-volatile memory.

The process of operation as illustrated in FIG. 7 includes steps of:

Step 530: storing the user's skin data as a written recipe or storing the data in a database. Such recipe or database may belong to the user, a health care professional, or a manufacturer.

Step 531: retrieving the user's skin data from the recipe or the data base.

Step 532: calculating for an optimal dispensing scheme. The user skin data, together with the specimen data of the specimen in the dispenser, are processed by a computer or a data processing unit not being part of the dispensing device, and an optimal dispensing scheme is formulated. The optimal dispensing scheme is hard coded into the dispenser, so that when specimen is dispensed from the dispenser, the specimen composition, timing or flow is following the optimal dispensing scheme. The hard code can be in the form of an electronic chip, a circuit component, a mechanical valve or a non-volatile memory.

Step 533: upon the specimen dispenser being installed into the dispensing device, dispensing the specimen from the dispenser. The device sends commands to the dispenser and dispenser dispenses specimen accordingly, or the device may directly drive the dispensing of specimen from the dispenser.

A cooling mechanism (not shown in FIG. 2) that cools the dispenser 14 can be implemented in the device 10. The mechanism provides cooling to the dispenser 14 or directly on the specimen 19 in the dispenser 14. It is controlled by the control unit 17. It can be, but not limited to, a thermoelectric cooling component utilizing the Peltier effect.

Further, a cooling mechanism that cools the specimen 19 can be configured within the dispenser 14. It can be, but not limited to, a thermoelectric cooling component utilizing the Peltier effect.

Although FIG. 1 and FIG. 2 show the dispenser 14 residing within the device body 11, in practice the dispenser 14 may also be externally attached to the device body 11.

Device 10 of FIG. 1 can be used as a stand-alone system, where its function does not depend on other extrinsic components function. Device 10 can also be used as an embedded system, where the function of the dispensing mechanism is an integral part of a larger system. For example, the device 10 of FIG. 1 can be used as a skin care product dispensing sub-system of a skin care device, where the surface 12 can also be a skin treatment member, which can deliver any or all of the physical means of, ultrasonic vibration, sub-sonic vibration, electrical voltage or current application, heating, cooling, light emission, air blowing, brushing, tapping, shaking, pulsating or scrubbing.

In the most preferred mode, the device body 11 of the device 10 is in an easy-holding palm-size oval shape and includes two continuous pieces—front and back pieces—which are mechanically coupled together. The specimen outlet 15 is on the front piece immediately coupled to the surface 12. In use, the back piece is for palm-holding. The device includes a wireless charger and thus it can be charged wirelessly. So, except the specimen outlet 15, the device does not have any other outlet or connectors.

Second Preferred Embodiment

Figure 8:
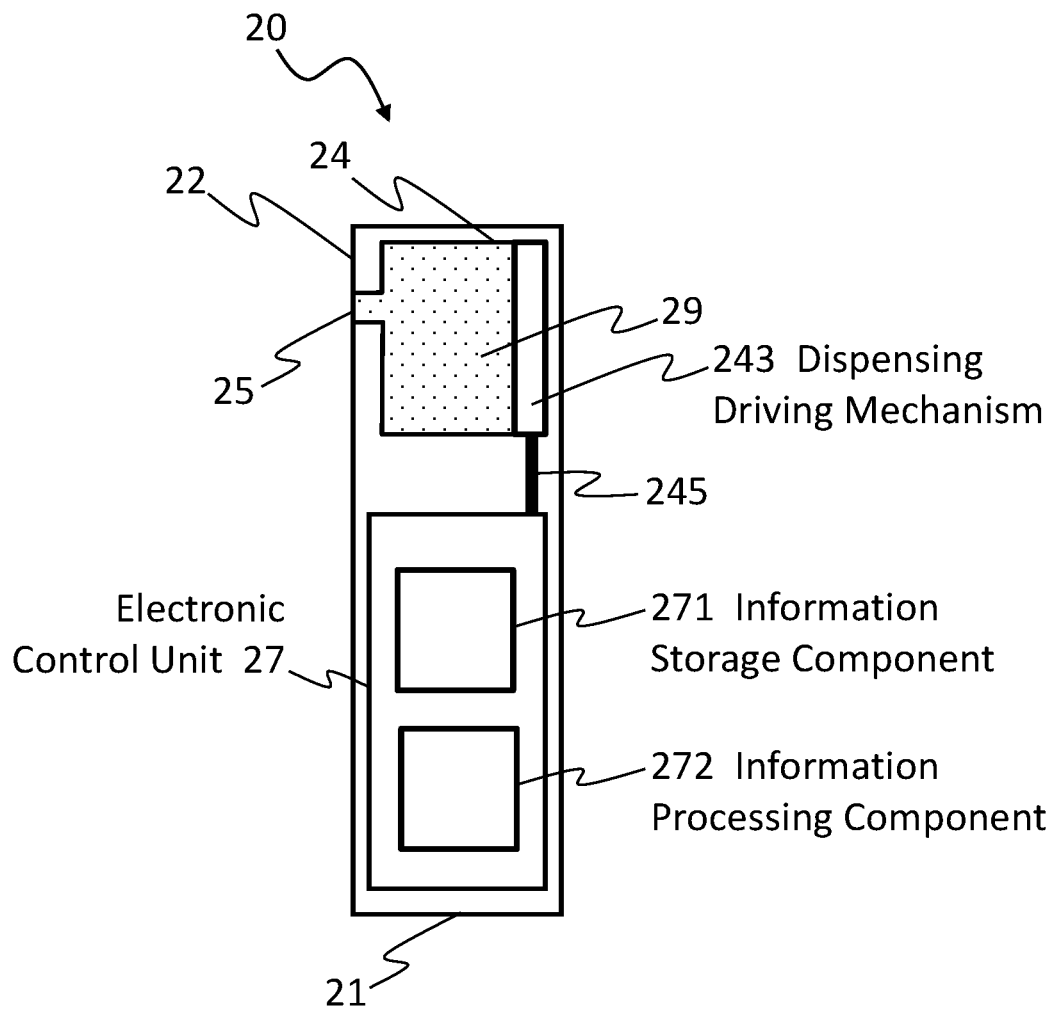
FIG. 8 is a schematic diagram illustrating a cross-sectional view of the specimen dispensing device according to the second preferred embodiment of the present invention.

FIG. 8 is a schematic diagram illustrating a cross-sectional view of a specimen dispensing device 20 according to the second preferred embodiment of the present invention, where a specimen dispenser is integrated within a specimen dispensing device 20. The components 21, 22, 24, 25, 27, 29, 271, and 272 in the second preferred embodiment as illustrated in FIG. 8 are substantially same as the components 11, 12, 14, 15, 17, 19, 171, and 172, respectively, as illustrated in FIG. 2.

However, the dispenser 24 does not include a digital data storage component. A dispensing driving mechanism 243 is coupled to the dispenser 24 to enable dispensing of the specimen 29. The control unit 27 has an information storage component 271 that contains specimen data of the specimen 29. Such specimen data can be recorded into the component 271 when the specimen dispenser 24 is integrated into the dispensing device 20. The recording of specimen data into the component 271 can be achieved electrically by an external data input device. The specimen data can also be automatically recorded into the component 271 by the control unit 27, when the dispenser 24 has non-electrical information containing feature, such as, but not limited to, indentation, protrusion, bar code, RFID, graphic or chemical, which triggers an information retrieval from such feature by the control unit 27. User skin data are imported into the device 20 and stored in the component 271. The information processing component 272 processes the specimen and user skin data from the component 271, and formulates an optimal dispensing scheme. The control unit 27 drives the dispensing mechanism 243 through the electrical interconnect 245 following the optimal scheme to dispense the specimen 29 from the dispenser 24.

Figure 9:
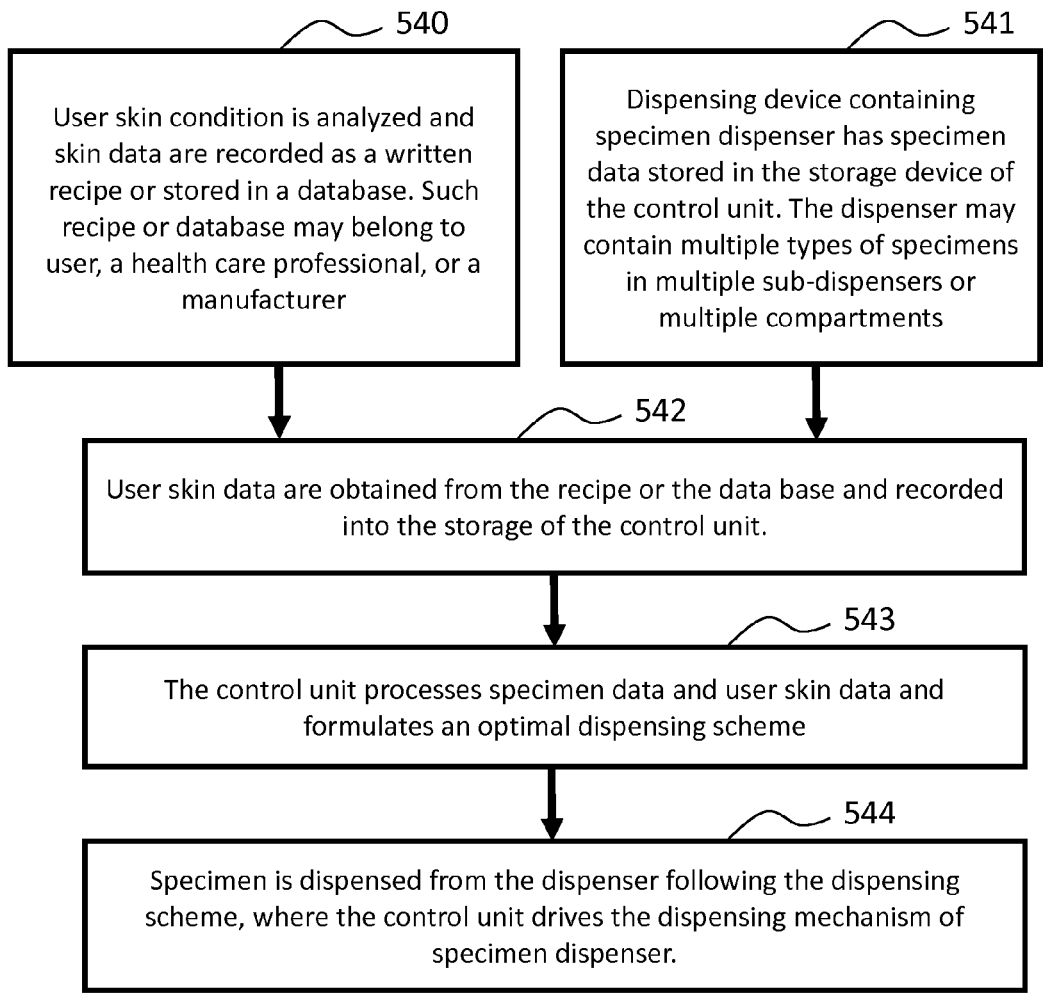
FIG. 9 is a flow diagram illustrating a process of operation of the specimen dispensing device according to the second preferred embodiment of the present invention.

A process of operation according to the second embodiment, as illustrated in FIG. 9, contains steps of:

Step 540: user skin condition is analyzed and skin data are recorded as a written recipe or stored in a database, wherein such recipe or database may belong to user, a health care professional, or a manufacturer.

Step 541: dispensing device containing specimen dispenser has specimen data stored in the storage device of the control unit, wherein the dispenser may contain multiple types of specimens in multiple sub-dispensers or multiple compartments.

Step 542: user skin data are obtained from the recipe or the data base and recorded into the storage of the control unit.

Step 543: the control unit processes specimen data and user skin data and formulates an optimal dispensing scheme.

Step 544: specimen is dispensed from the dispenser following the optimal dispensing scheme, where the control unit drives the dispensing mechanism of specimen dispenser.

A cooling mechanism (not shown in FIG. 8) that cools the dispenser 24 may be implemented in the device 20. The mechanism provides cooling to the dispenser 24 or directly on the specimen 29 in the dispenser 24. It is controlled by the control unit 27, and it can be, but not limited to, a thermoelectric cooling component utilizing the Peltier effect.

Further, a cooling mechanism that cools the specimen 29 within the dispenser 24 may be configured within the dispenser 24. It can be, but not limited to, a thermoelectric cooling component utilizing the Peltier effect.

Third Preferred Embodiment

Figure 10:
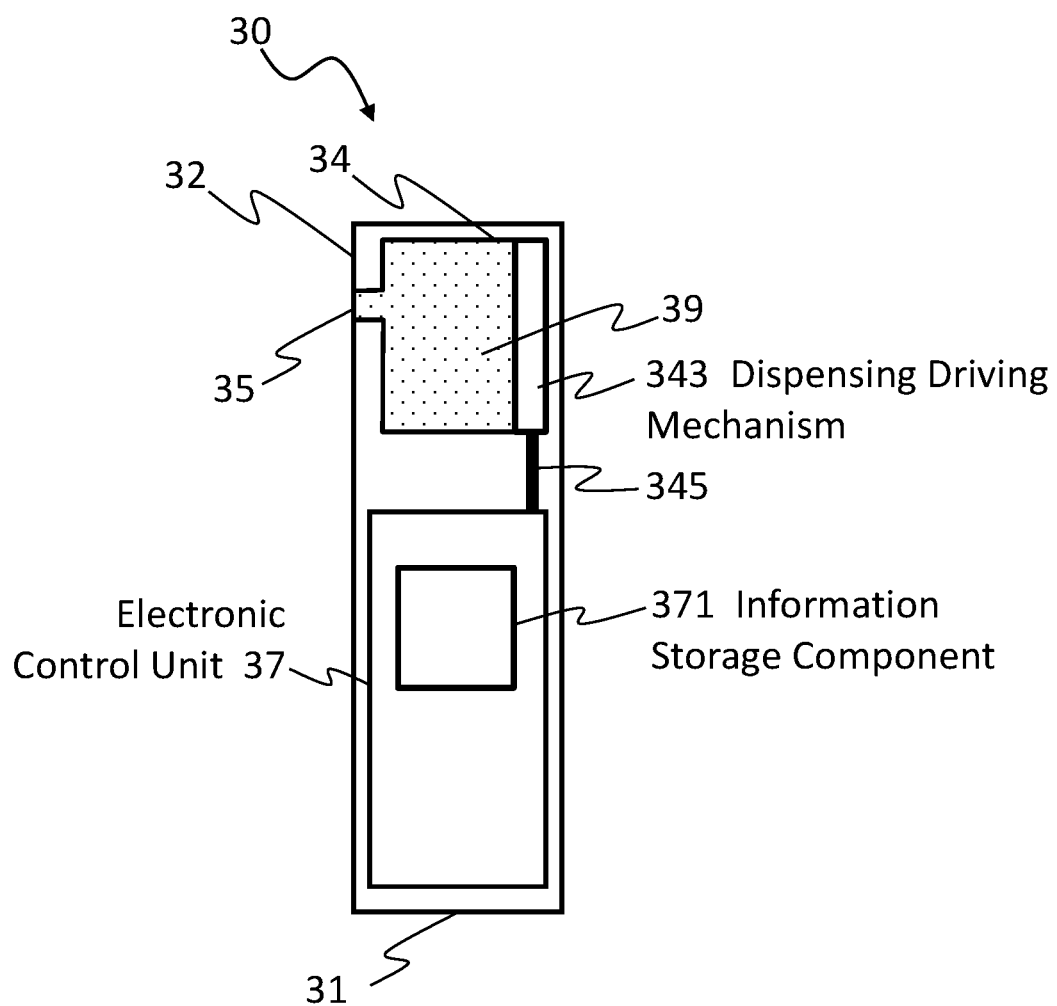
FIG. 10 is a schematic diagram illustrating a cross-sectional view of the specimen dispensing device according to the third preferred embodiment of the present invention.

FIG. 10 is a schematic diagram illustrating a cross-sectional view of the specimen dispensing device 30 according to the third preferred embodiment of the present invention, where a specimen dispenser is integrated within a specimen dispensing device 30. The components 31, 32, 34, 35, 37, 39, 343, and 345 in the third preferred embodiment as illustrated in FIG. 8 are substantially same as the components 21, 22, 24, 25, 27, 29, 243, and 245, respectively, as illustrated in FIG. 8.

The control unit 37 has an information storage component 371 that contains the information of the optimal dispensing scheme, with which the control unit 37 drives the dispensing mechanism 343 via an electrical interconnect 345 following the optimal scheme to dispense the specimen 39 from dispenser 34.

The optimal dispensing scheme is formulated outside of the dispensing device. Specimen data and skin data can be similarly stored in the component 371 as in the preferred second embodiment. They may also be stored external to the dispensing device 30. The specimen data and skin data are retrieved and processed by a computer or a data processing unit external for the dispensing device 30 to formulate an optimal dispensing scheme. This optimal dispensing scheme is then imported into the component 371. The control unit 37 reads the optimal scheme data from the component 371 and drives the dispensing mechanism 343 through the electrical interconnect 345 following the optimal scheme to dispense specimen 39 from the dispenser 34.

Figure 11:
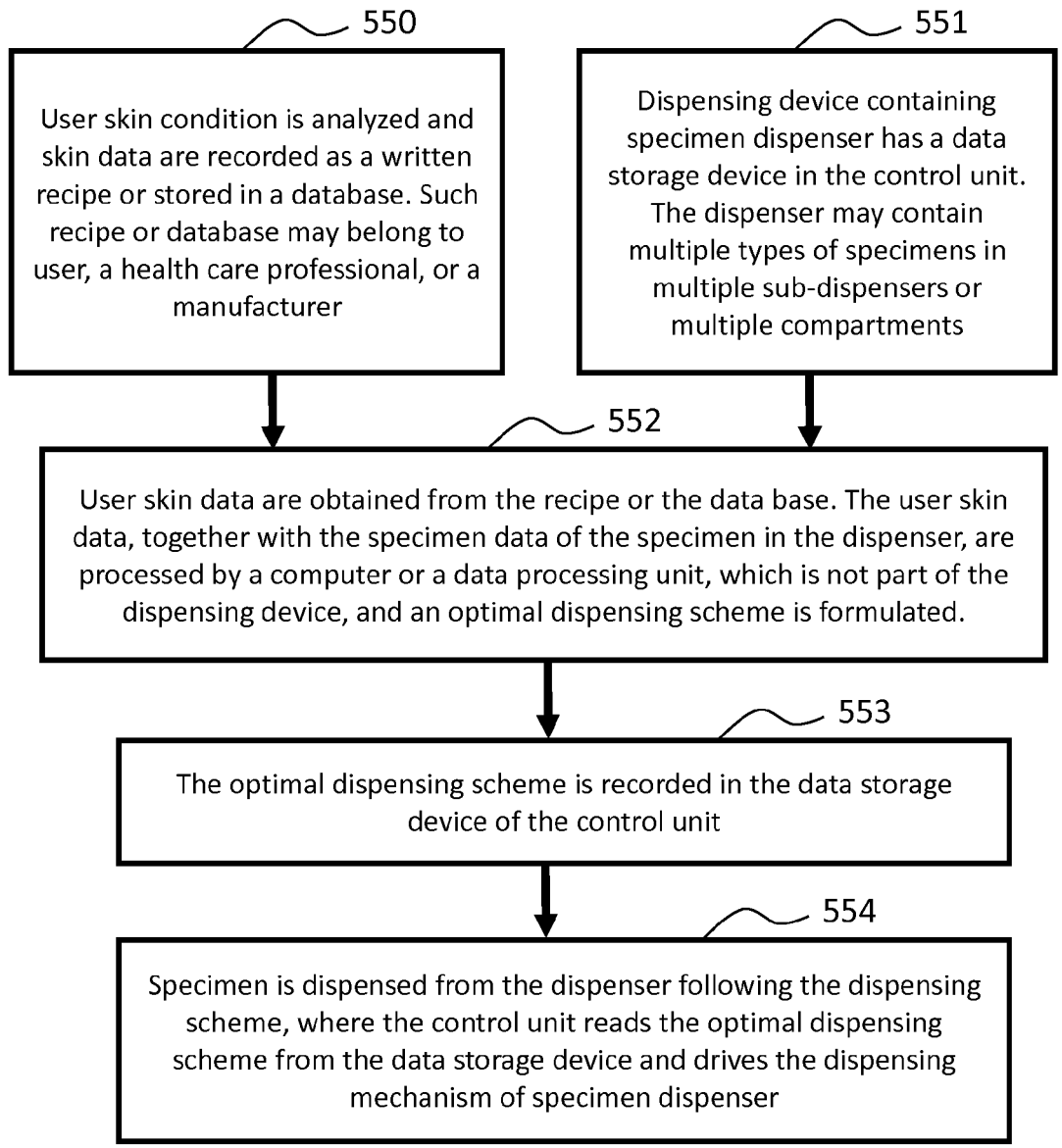
FIG. 11 is a flow diagram illustrating a process of operation of the specimen dispensing device according to the third preferred embodiment of the present invention.

A process of operation according to the second preferred embodiment, as illustrated in FIG. 11, includes the steps of:

Step 550: user skin condition is analyzed and skin data are recorded as a written recipe or stored in a database, wherein such recipe or database may belong to user, a health care professional, or a manufacturer.

Step 551: connecting the control unit with a data storage device associated with the control unit and with the specimen dispenser which may contain multiple types of specimens in multiple sub-dispensers or multiple compartments.

Step 552: retrieving the user skin data from the recipe or the data base and calculating for an optimal dispensing scheme. The user skin data, together with the specimen data of the specimen in the dispenser, are processed by a computer or a data processing unit, which is not part of the dispensing device, and an optimal dispensing scheme is formulated.

Step 553: storing the optimal dispensing scheme in the data storage device of the control unit.

Step 554: dispensing the specimen is from the dispenser following the optimal dispensing scheme, where the control unit reads the optimal dispensing scheme from the data storage device and drives the dispensing mechanism of specimen dispenser.

A cooling mechanism (not shown in FIG. 10) that cools the dispenser 34 can be implemented in the device 30. The mechanism provides cooling to the dispenser or directly on the specimen 39 in the dispenser 34. It is controlled by the control unit 37. It can be, but not limited to, a thermoelectric cooling component utilizing the Peltier effect.

Further, a cooling mechanism that cools the specimen 39 within the dispenser 34 may be configured in the dispenser 34. It can be, but not limited to, a thermoelectric cooling component utilizing the Peltier effect.

Fourth Preferred Embodiment

Figure 12:
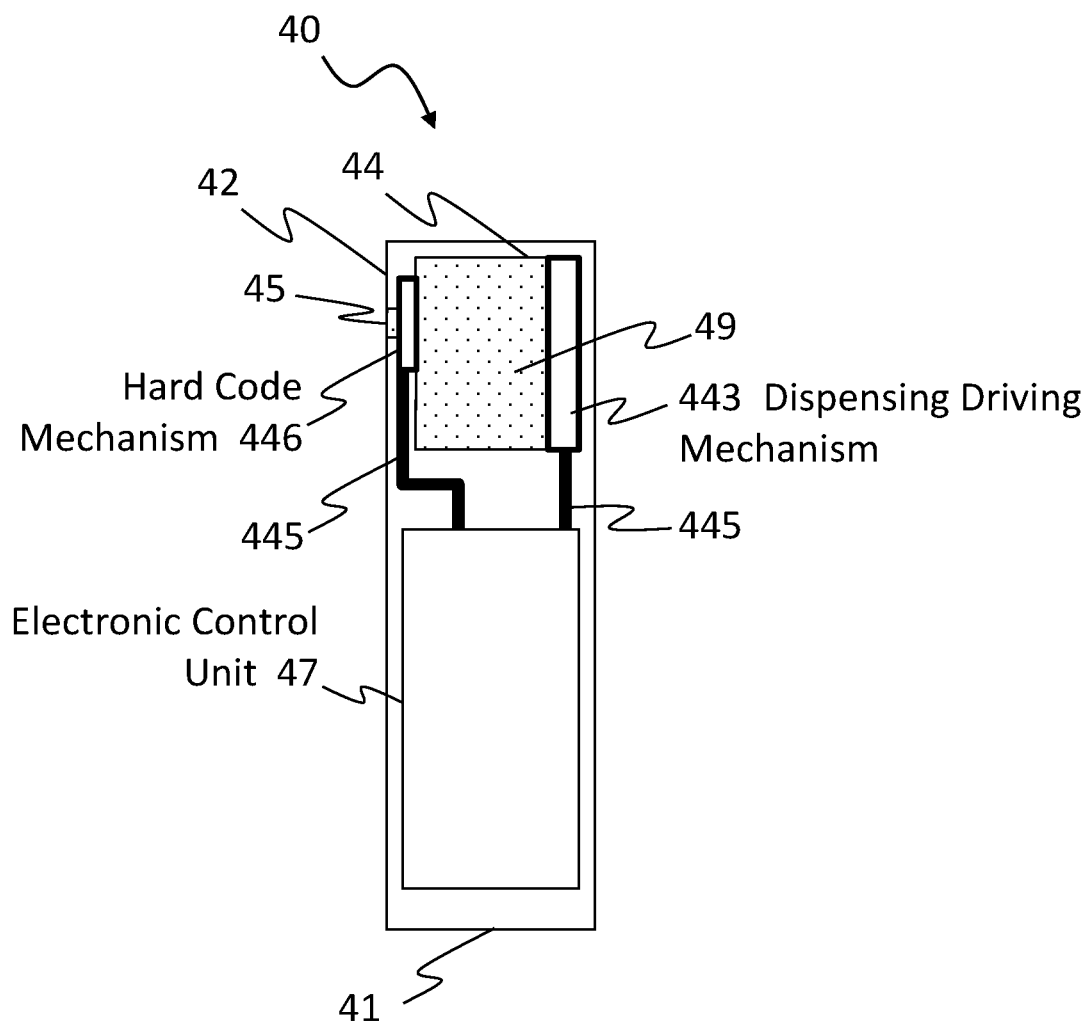
FIG. 12 is a schematic diagram illustrating a cross-sectional view of the specimen dispensing device according to the fourth preferred embodiment of the present invention.

FIG. 12 is a schematic diagram illustrating a cross-sectional view of the specimen dispensing device 40 according to the fourth preferred embodiment of the present invention, where a specimen dispenser is integrated within a specimen dispensing device 40. The components 41, 42, 44, 45, 47, 49, 443, and 445 in the fourth preferred embodiment as illustrated in FIG. 12 are substantially same as the components 21, 22, 24, 25, 27, 29, 243, and 245, respectively, as illustrated in FIG. 8.

However, the control unit 47 does not contain an information storage component. User skin data and specimen data are not stored in digital form within the dispensing device 40. The optimal dispensing scheme is hard coded into the dispensing mechanism, which regulates the specimen dispensing from the dispenser 44, or any sub-dispenser and any compartment of dispenser the 44, by any of: dispensed specimen composition, outflow speed and dispensing timing. Such hard coded dispensing mechanism is configured with considering both the specimen data, and the user data, user skin condition and any other type of information relating to the proper dispensing of the specimen to meet user skin care need. The hard code can be in the form of an electronic chip, a circuit component, a mechanical valve or a non-volatile memory.

The optimal dispensing scheme is formulated outside of the dispensing device 40. Specimen data and skin data are stored external to the dispensing device 40. The specimen data and skin data are retrieved and processed by a computer or a data processing unit external to the dispensing device 40 to formulate an optimal dispensing scheme. This optimal dispensing scheme is then transferred to the control unit 47, which then configures the hard code mechanism of the dispenser 446 through an electrical or a mechanical or a chemical or an optical interface 445. During dispensing, the control unit 47 drives the dispensing mechanism 443 through the electrical interconnect 445 following the optimal dispensing scheme to dispense the specimen 49 from the dispenser 44 to the device's treatment surface 42.

Figure 13:
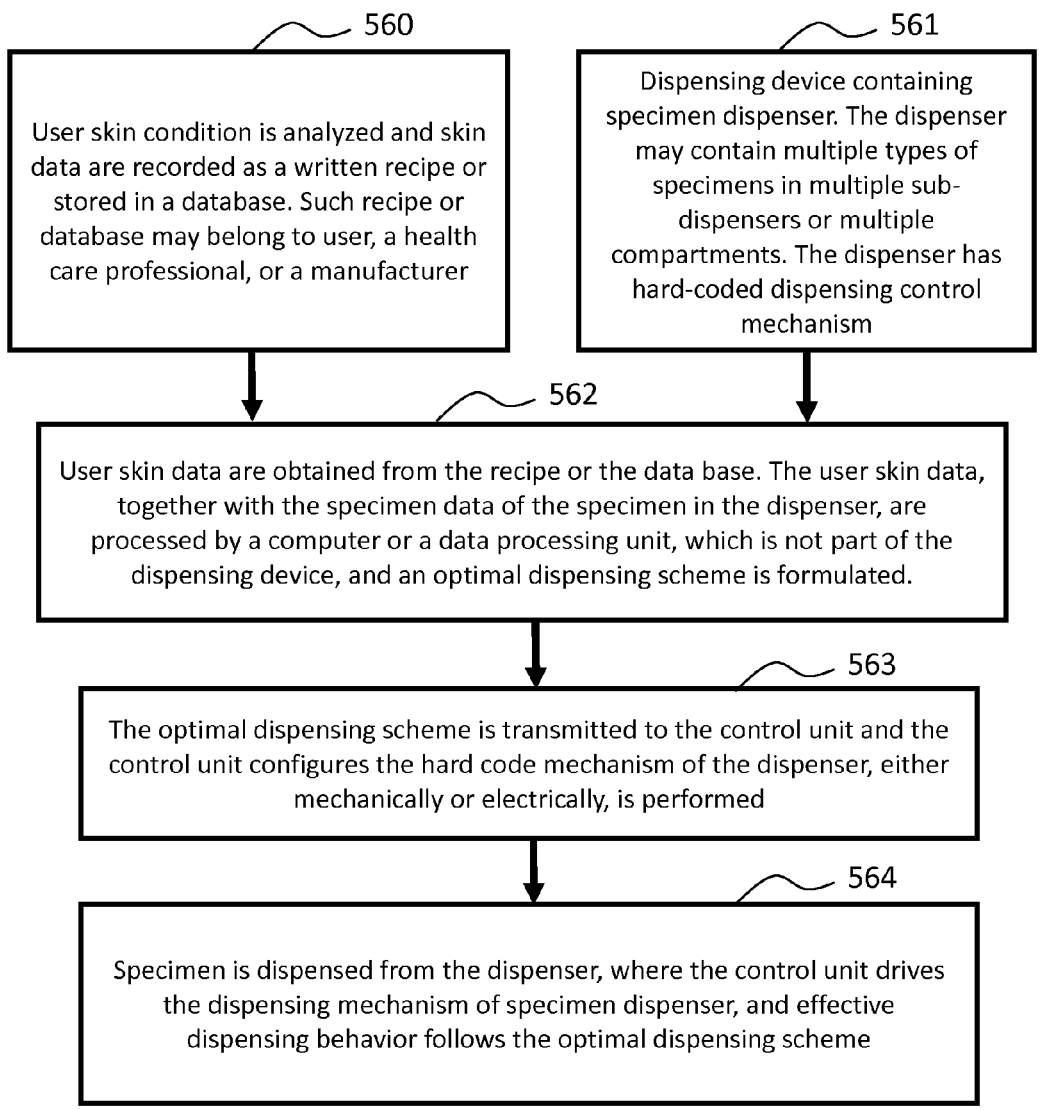
FIG. 13 is the flow of operation of the specimen dispensing device according to the fourth preferred embodiment of the present invention.

A process of operation according to the fourth preferred embodiment, as illustrated in FIG. 13, includes the steps of:

Step 560: User skin condition is analyzed and skin data are recorded as a written recipe or stored in a database, wherein such recipe or database may belong to user, a health care professional, or a manufacturer.

Step 561: installing the specimen dispenser into the dispensing device. The dispenser may contain multiple types of specimens in multiple sub-dispensers or multiple compartments. The dispenser has hard-coded dispensing control mechanism.

Step 562: calculating for an optimal dispensing scheme according to the user skin data retrieved from the recipe or the data base. The user skin data, together with the specimen data of the specimen in the dispenser, are processed by a computer or a data processing unit, which is not part of the dispensing device, and the optimal dispensing scheme is formulated.

Step 563: transmitting the optimal dispensing scheme to the control unit which configures the hard code mechanism of the dispenser, either mechanically or electrically.

Step 564: dispensing the specimen from the dispenser following the optimal dispensing scheme. The control unit drives the dispensing mechanism of the specimen dispenser, and effective dispensing behavior after modulation by the hard coded features follows the optimal dispensing scheme.

A cooling mechanism (not shown in FIG. 12) that cools the dispenser 44 can be implemented in the device 40. The mechanism provides cooling to the dispenser 44 or directly on the specimen 49 in the dispenser 44. It is controlled by the control unit 47. It can be, but not limited to, a thermoelectric cooling component utilizing the Peltier effect.

Further, a cooling mechanism that cools the specimen 49 within the dispenser 44 can be configured in the dispenser 44. It can be, but not limited to, a thermoelectric cooling component utilizing the Peltier effect.

Although the above description focuses on the application of the device 1 for skin care purpose, it is readily applicable for other health care and personal care needs, where device 10 can be used for dispensing personalized specimen for these other needs. Such needs can be, but not limited to, clinical usage to produce personalized drugs and medications, non-clinical usage for personalized recipes. The subject of treatment can be any biological body area, body function, organ, skin, bone, tissue or cell.

The advantages of the present invention are numerous. For examples, (1) the specimen dispensing device with electrical interface and embedded memory enables customizability of skin care products that are specifically tailored for each individual's own skin care need; and (2) with the electrical dispenser containing product information, best mode of operation, pre-set beautification process and usage data, the specimen dispensing device can greatly increase the treatment effect and user-manufacture interaction of the skin beautification process, reduces the complexity of the user's operation and provides means of feedback from user to manufacture for further improvement on the skin care products.

While one or more embodiments of the present invention have been illustrated above, the skilled artisan will appreciate that modifications and adoptions to those embodiments may be made without departing from the scope and spirit of the present invention.

The invention claimed is:

1. A method to produce customized specimens by using a specimen dispensing device which dispenses one or more specimens for purpose of treating a target skin area of a user comprising the steps of:
   analyzing skin condition of said user and obtaining user skin condition data;
   providing said specimen dispensing device that includes a removable dispenser and a control unit, said removable dispenser including said one or more specimens therein and a first information storage component storing first information, said control unit comprising a second information storage component storing second information and an information processing component that controls dispensing of said one or more specimens from said removable dispenser;
   storing said user skin condition data as part of said first information in said first information storage component in said removable dispenser; and
   dispensing said one or more specimens from said removable dispenser according to a dispensing scheme calculated from said first information stored in said first information storage component and said second information stored in said second information storage component.

2. The method of claim 1, wherein said removable dispenser is one of the following:
   a replaceable dispenser;
   a refillable dispenser;
   a disposable and for one-time use dispenser;
   a dispenser having multiple sub-dispensers containing same or different specimens, said sub-dispensers being individually selectable to dispense specimen therein; and
   a dispenser with multiple specimen compartments containing same or different specimens, each of said compartments being individually selectable to dispense specimen therein.

3. The method of claim 1, wherein said one or more specimens are dispensed from said removable dispenser by said control unit that controls dispensing of one or more specimens from one or more of compartments or sub-dispensers of said removable dispenser by a driving mechanism, said driving mechanism being a part of said removable dispenser or being coupled to said removable dispenser.

4. The method of claim 1, wherein said first information further includes one or more of the following:
information about said specimen;
information about optimal or pre-set operational mode of different sub-dispensers or difference specimen compartments within a single dispenser;
information about historic usage of said device, said removable dispenser and said specimen;
information that is created or input by a user, a manufacturer or a health care professional;
information transferred from said control unit;
biometrics information of a user; and
information for anti-counterfeit, anti-piracy and authenticity confirmation.

5. The method of claim 1, wherein each of said first and second information storage components includes one or more of the following:
a digital storage device;
an analog data storage device;
an optically recognizable markings;
an RF ID tag; and
physical indentations or protrusions.

6. The method of claim 1, wherein said second information includes one or more of the following: device operation data, user personal and biometrics information, dispenser identification data, date, time, season, weather and user specific data, application schedule and reminder message.

7. The method of claim 1, wherein said control unit performs one or more of the following:
receiving said first information stored in said first information storage component and said second information stored in said second information storage component;
processing said first and second information by said information processing component and providing instructions to control said removable dispenser to dispense said one or more specimens;
sending data to be stored in said first information storage component located in said removable dispenser;
providing user interface, power supply and charging functions; and
sending message wirelessly to one or more of the following devices: a computer, a mobile device, and a smart phone.

8. The method of claim 1, wherein said information processing component comprises embedded software for processing said first and second information,
wherein said embedded software, said first and second information are retrieved or updated through a data interface within said device;
wherein said retrieval and update is done by an external computing device; and
wherein said data interface includes one or more of the following:
a wireless transmitter/receiver within said control unit;
a data communication component utilizes a wireless charging circuitry to transmit digital or analog data; and
one or more electrical contacts that connect to said control unit.

9. The method of claim 1, wherein said first information is transmitted to said information processing component in said control unit by using a protocol,
wherein said protocol is configured such that different specimen information in a compartment or sub-dispenser of said removable dispenser is arranged in a same digital format;
wherein said same digital format is an ordered number and/or character sequence of information that contains an allocated space in said sequence; and
wherein said protocol is used in communication between said removable dispenser made by a first vendor and said dispensing device made by a second vendor.

10. A method to produce customized specimens by using a specimen dispensing device which dispenses one or more specimens for purpose of treating a target skin area of a user comprising the steps of:
analyzing skin condition of said user and obtaining user skin condition data;
storing said user skin condition data in a database;
providing said specimen dispensing device that includes a removable dispenser and a control unit, said removable dispenser including said one or more specimens therein and a first information storage component storing first information, said control unit comprising a second information storage component storing second information and an information processing component that controls dispensing of said one or more specimens from said removable dispenser;
acquiring said user skin condition data from said data base and storing said user skin condition data as part of said first information in said first information storage component in said removable dispenser; and
dispensing said one or more specimens from said removable dispenser according to a dispensing scheme calculated from said first information stored in said first information storage component and said second information stored in said second information storage component.

11. A method to produce customized specimens by using a specimen dispensing device which dispenses one or more specimens for purpose of treating a target skin area of a user comprising the steps of:
analyzing skin condition of said user and obtaining user skin condition data;
storing said user skin condition data in a database owned by a manufacturer of said one or more specimens;
providing said specimen dispensing device that includes a removable dispenser and a control unit, said removable dispenser including said one or more specimens therein and a first information storage component storing first information, said control unit comprising a second information storage component storing second information and an information processing component that controls dispensing of said one or more specimens from said removable dispenser by processing at least said second information;
acquiring said user skin condition data from said data base owned by said manufacturer and storing said user skin condition data as part of said first information in said first information storage component in said removable dispenser; and
dispensing said one or more specimens from said removable dispenser according to a dispensing scheme calculated from said first information stored in said first information storage component and said second information stored in said second information storage component.

* * * * *